United States Patent
Rannikko et al.

(10) Patent No.: US 6,900,058 B2
(45) Date of Patent: May 31, 2005

(54) CONTROL SOLUTION FOR PHOTOMETRIC ANALYSIS

(75) Inventors: Minna A. Rannikko, Millbury, MA (US); Donna M. Murray, Gardner, MA (US); Donna M. Rafferty, Ashburnham, MA (US)

(73) Assignee: Bionostics, Inc., Devens, MA (US)

( * ) Notice: Subject to any disclaimer, the term of this patent is extended or adjusted under 35 U.S.C. 154(b) by 0 days.

(21) Appl. No.: 10/387,115

(22) Filed: Mar. 11, 2003

(65) Prior Publication Data

US 2004/0180444 A1 Sep. 16, 2004

(51) Int. Cl.⁷ .............................................. G01N 31/00
(52) U.S. Cl. .............................. 436/14; 436/8; 436/15; 436/16; 436/18; 252/408.1
(58) Field of Search ................................ 436/8, 12–16, 436/18, 164, 166, 800; 435/14; 252/408.1

(56) References Cited

U.S. PATENT DOCUMENTS

| | | | |
|---|---|---|---|
| 3,920,580 A | * 11/1975 | Mast ............................ 436/14 |
| 4,373,932 A | 2/1983 | Gribnau et al. | |
| 4,729,959 A | * 3/1988 | Ryan ............................ 436/14 |
| 5,028,542 A | * 7/1991 | Kennamer et al. ............ 436/14 |
| 5,187,100 A | * 2/1993 | Matzinger et al. ............ 436/16 |
| 5,304,468 A | * 4/1994 | Phillips et al. ................ 435/14 |
| 5,306,623 A | * 4/1994 | Kiser et al. .................... 435/14 |
| 5,547,874 A | 8/1996 | Terashima | |
| 5,563,031 A | 10/1996 | Yu | |
| 5,605,837 A | * 2/1997 | Karimi et al. ................. 436/14 |
| 5,789,255 A | 8/1998 | Yu | |
| 5,866,349 A | 2/1999 | Lilja et al. | |
| 5,879,885 A | 3/1999 | Becker | |
| 5,910,109 A | 6/1999 | Peters et al. | |
| 5,932,428 A | 8/1999 | Dubrow et al. | |
| 5,998,501 A | * 12/1999 | Tsutsumi et al. ............ 523/160 |
| RE36,606 E | 3/2000 | Chriki | |
| 6,043,428 A | * 3/2000 | Han et al. .................... 136/263 |
| 6,059,561 A | 5/2000 | Becker | |
| 6,080,583 A | 6/2000 | Von Bahr | |
| 6,136,607 A | * 10/2000 | Conlon et al. ................. 436/8 |
| 6,162,397 A | * 12/2000 | Jurik et al. .................... 422/56 |
| RE37,053 E | 2/2001 | Hanes et al. | |
| 6,187,590 B1 | 2/2001 | Kim et al. | |
| 6,191,105 B1 | 2/2001 | Ekwuribe et al. | |
| 6,218,571 B1 | 4/2001 | Zheng et al. | |
| 6,251,581 B1 | 6/2001 | Ullman et al. | |
| 6,271,045 B1 | 8/2001 | Douglas et al. | |
| 6,350,582 B1 | 2/2002 | Baumgartner | |
| 6,362,003 B1 | 3/2002 | Young et al. | |
| 6,613,570 B2 | * 9/2003 | Knappe et al. ............... 436/14 |

FOREIGN PATENT DOCUMENTS

| | | |
|---|---|---|
| EP | 0 243 001 B1 | 10/1993 |
| EP | 0 595 846 B1 | 2/1997 |
| EP | 0 540 784 B1 | 1/2000 |
| WO | 95/13536 | * 5/1995 |

OTHER PUBLICATIONS

Web-based page from Sigma-Aldrich Catalog concerning Fluorescein Dibutyrate, product No. 46942, www.sigmaaldrich.com, no date.*

Blumberg, W. E., et al., "Hemoglobin Determined in 15 μL of Whole Blood by "Front–Face" Fluorometry", *Clin. Chem.*, 26(3):409–413 (1980).

Ghiggeri, G.M., et al., "Hydrophobic Interaction of Alcian Blue with Soluble and Erythrocyte Membrane Proteins", *Journal of Chromatography*, 452:347–357 (1988).

Baker, J., et al., "Fructosamine Test–Plus, a Modified Fructosamine Assay Evaluated", *Clin. Chem.*, 37(4):552–556 (1991).

* cited by examiner

*Primary Examiner*—Maureen M. Wallenhorst
(74) *Attorney, Agent, or Firm*—Hamilton, Brook, Smith & Reynolds, P.C.

(57) ABSTRACT

An aqueous control solution is disclosed for use with a spectrophotometer or photometric test strip that includes a predetermined amount of an analyte, a hydrophobic reference dye and a surfactant. In one embodiment, the aqueous control solution is applied to a photometric test strip having a chemical that oxidizes glucose and consequently forms hydrogen peroxide which reacts with an indicator dye that is also present on the strip. In this embodiment, the control solution includes a predetermined amount of glucose, an infrared reference dye, sodium dodecyl sulfate, and the indicator dye, such as sulforhodamine B.

9 Claims, 1 Drawing Sheet

CONTROL SOLUTION FOR PHOTOMETRIC ANALYSIS

BACKGROUND OF THE INVENTION

Accurate, reliable analyte detection in physiological fluids, such as whole blood, blood plasma, serum and urine, is becoming increasingly important for clinical diagnosis and management of diseases and conditions in humans and animals. For example, diabetes is typically diagnosed by determining whether the patient has abnormally high blood glucose levels, and once diagnosed, management of the disease often involves maintaining blood glucose levels within an acceptable range by dietary adjustments or medication. Studies have shown that careful control of blood glucose levels can significantly reduce the incidence of serious complications of diabetes such as vision loss, limb amputation and kidney failure.

In order to control blood glucose levels, some diabetics are required to test their blood glucose levels several times daily. Portable blood glucose meters are available which permit a patient to determine blood glucose levels quickly with a reasonable degree of accuracy. In general, these devices utilize disposable test strips that include chemicals that produce a color or electrochemical change, when a drop of a patient's blood is applied to the strip, in proportion to the amount of blood glucose present in the blood. For strips that change color, the strip bearing the patient's blood is inserted into the meter and the color change is measured using an optical reflectance system within the meter. The meter then generates a digital read-out corresponding to the concentration of glucose in the blood.

In order to obtain an accurate measurement of an analyte it is necessary to determine whether a spectrophotometer or reflectance meter is operating properly by, for example, measuring the amount of an analyte, such as glucose, that is present in a control solution that contains a predetermined (i.e., known) amount of the analyte. One problem encountered with control solutions for reflectance meters is that the dye used to produce the color change in response to the amount of analyte present tends to coalesce with other dye molecules. Dye coalescence increases with the length of time the control solution is on the test strip. This causes the analyte concentration reading to drift which leads to an inaccurate reading of analyte concentration. Thus, improvement in the stability of analyte concentration readings in control solutions is desirable.

In addition, optical reflectance meters provide accurate results only if the test strip is inserted into the meter properly and only if there is enough sample on a test strip. Since blood absorbs light at wavelengths around 940 nm, many meters are designed to detect absorbance of light at this wavelength. For an example of this type of meter see U.S. Pat. No. 5,605,837, the entire teachings of which are incorporated by reference. If the meter detects insufficient absorbance of light at this wavelength, an error warning informs the user that not enough blood was applied to the strip. In general, control solutions for such reflectance meters contain a substance that mimics the 940 nm blood absorbance of light so that the meter will inform the user when too little control solution has been applied to a test strip. In some control solutions, a suspension of particles, such as a suspension of carbon particles as is found in black india ink, has been used for this purpose. However, suspensions of carbon particles may precipitate out of solution to such an extent that the meter no longer recognizes that an appropriate amount of the control solution has been applied to a test strip. Therefore, it would be desirable to have an alternative means for simulating the absorption of light by blood at 940 nm in a control solution.

SUMMARY OF THE INVENTION

The invention provides control solutions for use with a spectrophotometer or photometric test strip. The aqueous control solutions include a predetermined amount of an analyte, a hydrophobic reference dye and a surfactant. The hydrophobic reference dye preferably has a maximum absorbance of light at a wavelength in the range of between about 700 nm to about 1100 nm so the control solutions of the invention mimic the light absorbance of whole blood.

In one embodiment, the aqueous control solution includes a predetermined amount of glucose, a dye with a molecular formula of $C_{62}H_{96}N_6SbF_6$ (an infrared dye which is commercially available from American Dye Source, catalog number ADS905AM), sodium dodecyl sulfate, and an indicator dye, such as sulforhodamine B or rose bengal. This control solution is used in conjunction with a reflectance meter which reads the amount of glucose in a sample that has been applied to a test strip. The test strip contains an enzyme or other chemical that oxidizes glucose and consequently forms hydrogen peroxide. The hydrogen peroxide then participates in an oxidation reaction where the indicator dye forms a reaction product that has an increased absorbance at a particular wavelength.

In one preferred embodiment, the aqueous control solution also includes a buffer such as a citrate buffer, an imidazole buffer, or a N-2-hydroxyethyl piperazine-N-2-ethanesulfonic acid buffer. In another preferred embodiment, the aqueous control solution contains a preservative such as diazolidinyl urea, 5-chloro-2-methyl-4-isothiazolin-one, 2-methyl-4-isothiazoline-3-one or combinations thereof. In another preferred embodiment, the aqueous control solution contains a viscosity enhancer, such as glycerol or polyvinylpyrrolidone.

The reference dye in the aqueous control solutions allows the user to determine whether the sample on the test strip is inserted properly in the instrument reading the color change of the sample, and in the case of photometric test strips indicates to the user whether sufficient sample has been applied to the test strip. In addition, the aqueous control solutions of the invention contain a surfactant which solublizes the hydrophobic reference dye and thus avoids precipitation problems of prior art control solutions. The surfactant also reduces coalescence of the indicator dye on the test strip, and thus reduces drift of analyte concentration readings.

DETAILED DESCRIPTION OF THE INVENTION

Figure 1:
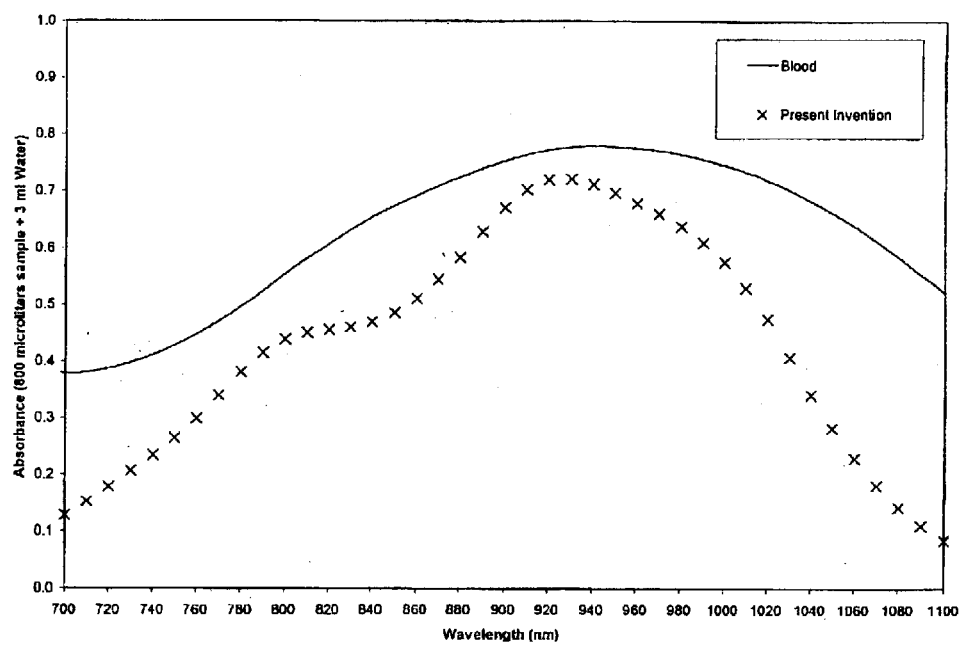
FIG. 1 is a graph showing the absorbance of leght for a control solution of the present invention (level 5, see Table 1 for formulation) and that of human blood (13.3 g/dL total hemoglobin).

A description of preferred embodiments of the invention follows.

An analyte, as used herein, is a material of interest in a physiological fluid, such as blood. Analytes of interest include glucose, cholesterol (high density, low density and total cholesterol), tryglycerides, fructosamine, amino acids, electrolytes ($Na^+$, $K^+$, and $Cl^-$), urea, uric acid, lactate, ketones, ketone bodies (acetoacetate and 3-hydroxybutyrate), hemoglobin, glycosylated hemoglobin, microalbumin, creatinine, metabolites related to disease, drugs and drug metabolites, pesticides, haptens and antigens (e.g., components of peptides, proteins, polysaccharides, nucleic acids, bacteria, viruses, chromosomes, genes, mitochondria, nuclei, cell membranes, and the like), and antibodies.

In a preferred embodiment, the analyte is glucose. Generally, glucose is present in a control solution of the invention in a concentration range of between about 10 mg/dL to about 500 mg/dL.

Drugs of interest as analytes include alkaloids, steroids, lactams, aminoalkylbenzenes, benzheterocyclics, purines, vitamins, prostaglandins, antibiotics, nucleosides, nucleotides, aminoglycosides, cannabinol and tetrahydrocannabinol.

Alkaloids include morphine alkaloids (e.g., morphine, codeine, heroin, and dextromethorphan), cocaine alkaloids (e.g., cocaine and benzoyl ecgonine), ergot alkaloids (e.g., diethylamide of lysergic acid), steroid alkaloids, iminazoyl alkaloids, quinazoline alkaloids, isoquinoline alkaloids, quinoline alkaloids (e.g., quinine and quinidine), diterpene alkaloids, and their derivatives and metabolites.

Steroid analytes include estrogens, estogens, progestogens, androgens, andreocortical steroids, bile acids, cardiotonic glycosides and aglycones (e.g., digoxin and digoxigenin), saponins and sapogenins, and their derivatives and metabolites. Steroid mimetic substances, such as diethylstilbestrol, are also drug analytes of interest.

Lactam analytes include barbituates (e.g., phenobarbital and secobarbital), diphenylhydantonin, primidone, ethosuximide, and their derivatives and metabolites.

Aminoalkylbenzenes analytes include amphetamines, catecholamines (e.g., ephedrine, L-dopa, epinephrine, narceine, papaverine), and their derivatives and metabolites.

Benzheterocyclic analytes include drugs that have an azepine, diazepine or phenothiazine heterocyclic ring, such as oxazepam, chlorpromazine, tegretol, imipramine, and their derivatives and metabolites.

Purine analytes include theophylline, caffeine, and their derivatives and metabolites.

Vitamin analytes of interest include A, B, $B_{12}$, C, D, K, folic acid and thiamine.

Antibiotic analytes include penicillin, chloromycetin, actinomycetin, tetracycline, teramycin, and their derivatives and metabolites.

Nucleoside and nucleotide analytes include adenosine triphosphate (ATP), nicotinamide adenine dinucleotide (NAD), flavin mononucleotide (FMN), adenosine, guanosine, thymidine, and cytidine, and their derivatives and metabolites.

Other drug analytes of interest include methadone, meprobamate, serotonin, meperidine, amitriptyline, nortriptyline, lidocaine, procaineamide, acetylprocaineamide, propanolol, griseofulvin, valproic acid, butyrophenones, antihistamines, anticholinergic drugs (e.g., atropine), and their derivatives and metabolites.

Metabolites related to disease states which may be analytes of interest include spermine, galactose, phenylpyruvic acid, and porphyrin.

Pesticides of interest include polyhalogenated biphenyls, phosphate esters, thiophosphates, carbamates, polyhalogenated sulfonamides, and their derivatives and metabolites.

An indicator dye, as used herein, is a compound that produces an increase in absorbance of a particular wavelength of light (e.g., a color intensity change) in proportion to the amount of an analyte present in a control solution or in a physiological sample. Thus, the amount of analyte in the control solution or physiological sample can be measured by measuring the change in absorbance of the indicator dye, or chemical derivative of the indicator dye, when the indicator dye is contacted by a sample containing the analyte. The concentration of many analytes (e.g., acetaminophen, salicylate, creatinine, cholesterol, triglycerides, glucose and uric acid) can be determined by using enzymes that generate hydrogen peroxide when they interact with the analyte; the hydrogen peroxide subsequently can be assayed by way of peroxidase-coupled redox chemistry (see Arter, et al., EPO application No. 93111290.8, published on Jan. 19, 1994, the entire teachings of which are incorporated herein by reference). For example, one commonly employed glucose detection system includes glucose oxidase, horseradish peroxidase, meta-(3-methyl-2-benzothiazolinone hydrazone)-N-sulfonyl benzenesulfonate monosodium (MBTHSB) and 8-(anilino)-1-naphthalenesulfonate (ANS). In this system glucose oxidase interacts with glucose in a sample in the presence of oxygen to produce hydrogen peroxide. Horseradish peroxidase catalyzes the oxidation of MBTHSB by hydrogen peroxide. The oxidized form of MBTHSB oxidizes ANS (the indicator dye in this system) to produce a compound that absorbs yellow light (580–595 nm) and thus produces a blue color. This light absorbance can be used to determine the amount of glucose in the sample.

The control solutions of the invention optionally contain an indicator dye. Alternatively, the indicator dye can be present on a test strip which is contacted with the control solution. Indicator dyes which optionally may be present in the control solutions of the invention include rose bengal, sulforhodamine (SRA), amaranth, ANS and derivatives thereof. Typically, when an indicator dye is present in a control solution of the invention, it is present in a concentration range of between about 0.25 g/L to about 2.0 g/L.

A hydrophobic reference dye is a dye compound that is soluble in hydrophobic solvents but is generally insoluble in aqueous solutions. However, in the aqueous control solutions of this invention, these hydrophobic reference dyes can be solubilized by adding a surfactant to the solution. The hydrophobic reference dye of this invention typically does not readily absorb light in a region of the electromagnetic spectrum where the indicator dye has a high extinction coefficient after reaction with the analyte in the sample.

Since blood absorbs light in the infrared region of the electromagnetic spectrum (about 940 nm), the reference dye preferably absorbs light in this region, particularly when the physiological sample containing the analyte of interest is blood. In a preferred embodiment, the hydrophobic reference dye absorbs light in the range of between about 700 nm to about 1100 nm. Preferred hydrophobic reference dyes include $C_{62}H_{96}N_6SbF_6$ (an infrared dye which is commercially available from American Dye Source, catalog number ADS905AM), $C_{62}H_{92}Cl_2N_6O_8$ (an infrared dye which is commercially available from H. W. Sands, catalog number SDA8080), and $C_{62}H_{92}N_6SbF_6$ (an infrared dye which is commercially available from H. W. Sands, catalog number SDA5324). The hydrophobic reference dye is typically present in an amount that will give an absorbance reading on a spectrophotometer in a range of between about 0.1 to about 2.5. Control solutions that have this range of hydrophobic reference dye absorbance are typically suitable for use with optical meters that work on light reflectance from a sample on a test strip.

A surfactant, as used herein, is a compound that reduces the surface tension between two liquids. In the control solutions of the invention, one or more surfactants are present, typically in a concentration range of between about 1 g/L to about 20 g/L, preferably between about 1 g/L and 15 g/L. Surfactants cause the hydrophobic reference dye to remain in solution in the aqueous control solutions of the invention. In addition, surfactants in the control solutions of the invention reduce coalescence of the indicator dye, particularly on a test strip, and, thus, reduce drift of analyte concentration readings. Typically, a surfactant has a hydrophobic group and a hydrophilic group. The hydrophobic group is usually an aliphatic hydrocarbon residue having from 10 to 20 carbon atoms or an alkylbenzene residue. The hydrophilic group increases the solubility of the surfactant in water and can be selected from a variety of groups such as a carboxylic acid, $-OSO_3H$, $-SO_3H$, ethers, and polyether groups such as $-(R-O)_n-R_1$, wherein n is an integer, and R and $R_1$ are each, independently, an aliphatic or aromatic group. Common families of surfactants include sodium alkyl sulfate, bile acid surfactants, sulfobetaines, and alkylglucosides.

Surfactants can be classified as anionic, cationic, amphoteric or non-ionic. Anionic surfactants include sodium dodecyl sulfate, ammonium perfluoralkyl carboxylate, sodium lauroyl myristoyl lactylate, glycocholic acid, cholic acid, taurocholic acid, deoxycholic acid, glycodeoxycholic acid, taurodeoxycholic acid, amine alkylbenzene sulfonate, sodium dioctylsulfosuccinate, sodium olefin sulfonate, and sodium polyoxyethylene(1) lauryl sulfate.

Cationic surfactants include coco hydroxyethyl imidazoline, lauryltrimethylammonium chloride, decyltrimethylammonium bromide, octyltrimethylammonium bromide, and cetyl trimethyl ammonium bromide.

Amphoteric surfactants include N-dodecyl-N,N-dimethylglycine, lauramidopropyl betaine, N-tetradecyl-N,N-dimethyl-3-ammonio-1-propanesulfonate, N-dodecyl-N,N-dimethyl-3-ammonio-1-propanesulfonate, cocoamidopropylbetaine, cocoamidosulfobetaine, N-octyl-N,N-dimethyl-3-ammonio-1-propanesulfonate, and N-tetradecyl-N,N-dimethyl-3-ammonio-1-propanesulfonate.

Non-ionic surfactants include dodecyl-β-D-maltoside, N,N-bis(3-D-glucon-amidopropyl) cholamide, polyoxypropylene-polyoxyethylene block copolymer, N-tetradecyl-β-D-maltoside, daconyl-N-methyl-glucamide, hexyl-β-D-glucopyranoside, heptyl-β-D-glucopyranoside, octyl-β-D-glucopyranoside, nonyl-β-D-glucopyranoside, decyl-β-D-glucopyranoside, dodecyl-β-D-glucopyranoside, octyl-β-D-thioglucopyranoside, polyethylene glycol ester of stearic acid, ethoxylated cocomonoglyceride, octyphenoxy-poly (ethyleneoxy) ethanol, ethoxylated octylphenol, and polyoxyethylene alkyl ethers.

Salts of surfactants containing acidic functional group can be prepared by, for example, reacting the surfactant with a suitable base. Such salts may be made with a base which affords a cation, such as alkali metal salts (especially sodium and potassium), alkaline earth metal salts (especially calcium and magnesium), aluminum salts and ammonium salts. These salts may be prepared by methods known to those skilled in the art.

Salts of surfactants containing a basic group can be obtained by reacting the surfactant with a suitable organic or inorganic acid, such as hydrogen chloride, hydrogen bromide, acetic acid, perchloric acid and the like. Surfactants with a quaternary ammonium group also contain a counteranion such as chloride, bromide, iodide, acetate, perchlorate and the like. Other examples of such salts include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures), succinates, benzoates and salts with amino acids such as glutamic acid.

An aliphatic group, as used herein, means straight-chain, branched or cyclic $C_1$–$C_{20}$ hydrocarbons which are completely saturated or which contain one or more units of unsaturation but which are not aromatic. For example, suitable aliphatic groups include substituted or unsubstituted linear, branched or cyclic alkyl, alkenyl, alkynyl groups and hybrids thereof such as (cycloalkyl)alkyl, (cycloalkenyl) alkyl or (cycloalkyl)alkenyl. The term "cycloalkyl" used alone or as part of a larger moiety shall include cyclic $C_3$–$C_{20}$ hydrocarbons which are completely saturated or which contain one or more units of unsaturation, but which are not aromatic.

As used herein, aromatic groups are carbocyclic aromatic ring systems (e.g., phenyl), fused polycyclic aromatic ring systems (e.g., naphthyl and anthracenyl) and aromatic ring systems fused to carbocyclic non-aromatic ring systems (e.g., 1,2,3,4-tetrahydronaphthyl) having six to about twenty carbon atoms.

An antifoaming agent, as used herein, is a compound that inhibits the formation of bubbles in a liquid during agitation of the liquid. Antifoaming agents include silicones, organic phosphates and alcohols. Preferred antifoaming agents are dimethyl siloxanes, methyl cellulose, hydrogenated tallow glycerides, and silicone polymers. One or more antifoamings agent may be used in the control solutions of the invention. When an antifoaming agent is present in a control solution of the invention, it is typically present in a range of between about 1.0 g/L to about 0.01 g/L.

One or more preservatives may be used in the control solutions of the invention. A preservative is a compound that inhibits the growth of bacteria in the solution, such as sodium benzoate, potassium benzoate, benzalkonium chloride, chlorhexidine, imidazolidinyl urea, diazolidinyl urea (also called Germall II), 5-chloro-2-methyl-4-isothiazolin-3-one, and 2-methyl-4-isothiazolin-3-one. Preferred preservatives are diazolidinyl urea, 5-chloro-2-methyl-4-isothiazolin-3-one, and 2-methyl-4-isothiazolin-3-one or a mixture thereof. A particularly preferred preservative is a mixture of 5-chloro-2-methyl-4-isothiozalin-3-one (2.3%), 2-methyl-4-isothiazolin-3-one (0.7%), plus inert ingredients modified glycol (93–95%) and alkylcarboxylate (2–3%), known collectively as ProClin 300. When a preservative is present in a control solution of the invention, it is typically present in a concentration range of between about 0.5 g/L to about 2.0 g/L.

A chelator, as used herein, is an organic compound the atoms of which form more than one coordinate bond with one or more metals in solution. A chelator can be added to the control solutions of the invention to bind metals that may react with glucose or the dye. In addition, chelators bind calcium, thereby aiding the inhibition of microbial activity. Examples of chelators include ethylenediaminetetraacetic acid (EDTA), citric acid, and salts thereof. Salts of chelators can be formed in the same manner as salts of surfactants having an acidic group. When a chelator is present in a control solution of the invention, it is typically present in a concentration range of between about 0.01 mM to about 100 mM.

A viscosity enhancer can be used in the control solutions of the invention, particularly when the control solution is to be used in conjunction with a test strip and a reflectance meter. When the control solution is used to verify the accuracy of a reflectance meter that utilizes a test strip, the viscosity of a control solution can be important for three reasons. First, if flow of the control solution were to continue unimpeded, gravity would cause excess fluid to accumulate on the lower surface of the membrane of the test strip where the reflectance reading takes place. This excess fluid can impede accurate reflectance measurements of the developed color on the reading surface. Second, continued delivery of an analyte to the reagent system can result in increasing color intensity as long as the flow continues. However, if the flow of control solution is stopped upon reaching the reading surface of the test strip, the analyte sample size is controlled and the color variation ceases when the analyte has completely reacted with the reagents in the test strip. Third, in the absence of a flow controlling factor, the control solution will be drawn into the membrane surrounding the sample application zone of the test strip, carrying with it reagents and developed dyes and depleting the concentration of these chemicals in the center of the application zone, thereby creating an inhomogeneous pattern of analyte detection. Viscosity enhancers can be used to increase the viscosity of the control solution so that each of these problems are minimized. Examples of viscosity enhancers are glycerol, polyvinylpyrrolidone (PVP) and starch.

The control solutions of the invention can also include a buffer to maintain the pH of the control solution relatively constant. Typically, control solutions of the invention have a pH in the range of between about 4.5 to about 8.0. Preferably, the pH is maintained within the pH range of about 5.0 to about 7.3. The particular buffer used will depend upon the desired pH range of the control solution. In a preferred embodiment, the buffer includes citric acid and a citric acid salt. This buffer is typically used when it is desirable to maintain the pH of the control solution within a range of about 5.0 to about 5.5. In another preferred embodiment, the buffer is a N-2-hydroxyethyl-piperazine-N-2-ethanesulfonic acid (HEPES). This buffer is typically used when it is desirable to maintain the pH of the control solution within a range of about 6.7 to about 7.3. In another preferred embodiment, the buffer is an imidazole buffer.

The following examples are presented to illustrate the invention and are not intended to limit the scope of the invention in any way.

EXAMPLES

Five control solutions were prepared having varying amounts of glucose. The ingredients for each formulation are listed in Table 1. The ingredients were mixed with an initial amount of deionized water for at least 1 hour, then brought to 1 L with deionized water. If necessary the pH was adjusted with HCl. Each solution was passed through a 0.2 µm PES filter (Corning P/S431097 or equivalent).

TABLE 1

Control Solution Formulations (all units are in grams)

| Chemical | Level 1 | Level 2 | Level 3 | Level 4 | Level 5 |
| --- | --- | --- | --- | --- | --- |
| Initial High Purity Water | 100 | 500 | 500 | 500 | 500 |
| glycerol | 12 | 12 | — | — | 4.0 |
| Trisodium Citrate | 8.0 | 8.0 | — | — | — |
| Citric Acid, Anhydrous | 1.0 | 1.0 | — | — | — |
| Germall II | 2.0 | 2.0 | — | — | — |
| Sodium Dodecyl Sulfate | 1.3 | 9.0 | 15 | 15 | 15 |
| Glucose | 0.33 | 0.74 | 1.33 | 1.74 | 2.12 |
| PVP 9,000 | — | 3.75 | 10.0 | 10.0 | 10.0 |
| ADS905AM | 0.19 | 0.14 | 0.09 | 0.08 | 0.07 |
| HEPES acid | — | — | 2.38 | 2.38 | 2.38 |
| NaOH | — | — | 0.26 | 0.27 | 0.27 |
| EDTA, disodium | — | — | 1.5 | 1.5 | 1.5 |
| SRA B, acid form | 0.25 | 0.25 | 0.25 | 0.25 | 0.25 |
| ProClin 300 | — | — | 0.5 | 0.5 | 0.5 |
| Final pH | 5.3–5.8 | 5.3–5.8 | 6.7–7.3 | 6.7–7.3 | 6.7–7.3 |

Glucose Values

LifeScan SureStep® Pro test strips are designed to measure levels of glucose in a sample. Control solutions for LifeScan SureStep® Pro test strips are formulated to have glucose concentrations which correspond to the midpoint of five glucose ranges. Each of these glucose concentrations can be measured by Lifescan SureStep® Pro test strips. The glucose range of control solutions levels 1 to 5 of Table 1 were formulated to correspond to glucose values of levels 1 to 5 of commercial LifeScan SureStep® Pro control solutions. Glucose values for control solution levels 1 to 5 of Table 1 were measured using a SureStep® Pro test strip at 20° C., 25° C. and 34° C. at ambient humidity. The results of these measurements are shown in Table 2. The measured glucose concentrations were all within the expected range of values.

TABLE 2

Glucose Mean Results (n = 5)

| Level | Strip Glucose Range (mg/dL) | Strip Glucose Target (mg/dL) | Temp. = 20° C. Measured Glucose (mg/dL) | Temp. = 25° C. Measured Glucose (mg/dL) | Temp. = 34° C. Measured Glucose (mg/dL) |
| --- | --- | --- | --- | --- | --- |
| 1 | 32–56 | 44 | — | 41 | 43 |
| 2 | 90–134 | 112 | 105 | 112 | 118 |
| 3 | 191–285 | 238 | 229 | 238 | 236 |
| 4 | 274–410 | 342 | 309 | 339 | 305 |
| 5 | 352–500 | 439 | 406 | 420 | 410 |

Glucose Precision

Based on the printed range on LifeScan SureStep® Pro test strip bottles (Table 2, Column 2), it is desirable to have a measured glucose range within ±12 mg/dL of the glucose midpoint for control solution level 1. For control solution levels 2 through 5, it is desirable to have a measured glucose range within ±20% of the glucose midpoint of these control solutions. The control solutions, levels 1 through 5, of the invention meet these specifications.

Precision of glucose measurements for control solutions levels 1 to 5 of the invention were further evaluated using SureStep® Pro test strips. Five samples were measured on each of 5 separate meters. Table 3 summarizes precision data for glucose control solutions levels 1 to 5 of the invention. As a comparison to the control solutions of the invention, LifeScan reports precision values with their control solutions ranging from 3% to 5% Coefficient of Variation (CV).

TABLE 3

Glucose Precision Results (n = 25)

| Level | Glucose Precision (% CV) |
|---|---|
| 1 | 3.1 |
| 2 | 2.2 |
| 3 | 4.5 |
| 4 | 5.7 |
| 5 | 4.3 |

Performance of Control Solution on Test Strip

In addition to formulating control solution levels 1 through 5 with specific glucose target concentrations, the control solutions in Table 1 were also formulated to have other desirable properties as described below.

As discussed previously, many meters are designed to detect a reduction in radiation at about 940 nm since blood absorbs light at this wavelength. If the meter detects insufficient reduction in radiation at this wavelength, an error warning informs the user that not enough blood was applied to the test strip. The control solutions of the invention, as shown in Table 1, have been formulated to mimic blood absorption of light having a wavelength of 940 nm so that such a meter will inform the user when too little control solution has been applied to a test strip. Thus, the control solutions in Table 1 contained reference dye $C_{62}H_{96}N_6SbF_6$ (American Dye Source, catalog number ADS905AM) which has a maximum absorbance at 905 nm. Hydrophobic dyes having an absorbance maximum in the range of between about 700 nm to about 1100 nm are preferred reference dyes in control solutions of the invention as long as they do not absorb light significantly in a region of the electromagnetic spectrum where the indicator dye absorbance changes in response to the amount of analyte in a sample (see FIG. 1). Other dyes which can be used when glucose is the analyte of interest include $C_{62}H_{92}Cl_2N_6O_8$ (H. W. Sands, catalog number SDA8080), and $C_{62}H_{92}N_6SbF_6$ (H. W. Sands, catalog number SDA5324). The absorbance amount at 940 nm needed for the meter to recognize the control solution depends upon the meter used. For a SureStep® Meter, if the absorbance at 940 nm is not adequate, an error message will be displayed on the meter. The control solutions in Table 1 were formulated to have sufficient absorbance at 940 nm within this range. Table 4 shows the absorbance at 940 nm for control solution levels 1 through 5 of Table 1 using a SureStep® Pro test strip and a SureStep® Meter. Low temperature readings (about 20° C.) and high temperature readings (34° C.) were taken on each test strip for each level of control solution. As can be seen from Table 4, the absorbance at 940 nm for each control solution is between about 0.7 and about 1.9. Additionally, the control solutions have very little absorbance at about 660 nm to avoid interference with the wavelength of light used for measuring glucose.

Another parameter of importance is the endpoint time. As described above, the amount of an analyte in a physiological sample or a control solution is typically determined by a chemical or enzymatic reaction of the analyte with reagents which thereby increases the absorbance of the indicator dye at a particular wavelength. Generally, the chemical or enzyme which reacts with the analyte is on the test strip. The endpoint time is the elapsed time from when the test strip is contacted with the physiological sample or control solution and the time at which the absorbance of the indicator dye no longer increases. A short endpoint time is desirable because it provides more immediate results for the user and reduces the possibility of an inaccurate measurement of analyte concentration caused by reading the analyte concentration before the reaction endpoint has been reached. As can be seen from Table 4, the endpoint times for control solution levels 1 through 5 of Table 1 were less than 60 seconds at 24° C.

Once the endpoint of the indicator reaction has been reached, it is desirable for the absorbance of the indicator dye to remain relatively constant (e.g., less than 10% change) for at least 2 minutes so that a user will have sufficient time to insert the test strip into the meter. As discussed above, one problem encountered with control solutions for reflectance meters is that the dye which produces the color change in response to the amount of analyte present tends to coalesce with other dye molecules. Dye coalescence increases with the length of time the control solution is on the test strip, thereby causing the analyte concentration reading to drift. As can be seen from Table 4, endpoint glucose values were within 10% of the glucose values obtained when the test strips were inserted into the meter 2 minutes after application of the control solution.

TABLE 4

Control Solution Strip Performance (n = 5) at 24° C.

| Level | Absorbance at 660 nm | Absorbance at 940 nm | Endpoint time (sec) | Endpoint Glucose vs. 2 minute Glucose (% Drift) |
|---|---|---|---|---|
| 1 | 0.2 | 1.9 | 29 | 7 |
| 2 | 0.1 | 1.8 | 35 | 5 |
| 3 | 0.1 | 0.9 | 40 | 9 |
| 4 | 0.1 | 0.8 | 51 | 7 |
| 5 | 0.1 | 0.7 | 59 | 3 |

While this invention has been particularly shown and described with references to preferred embodiments thereof, it will be understood by those skilled in the art that various changes in form and details may be made therein without departing from the scope of the invention encompassed by the appended claims.

What is claimed is:

1. An aqueous control solution, comprising a predetermined amount of glucose, $C_{62}H_{96}N_6SbF_6$, sodium dodecyl sulfate, and an indicator dye selected from the group consisting of sulforhodamine B and rose bengal.

2. The solution of claim 1, further comprising a preservative.

3. The solution of claim 2, wherein the preservative is selected from the group consisting of diazolidinyl urea, sodium benzoate, potassium benzoate, benzalkonium chloride, chlorhexidine, imidazolidinyl urea, 5-chloro-2-methyl-4-isothiazolinone, 2-methyl-4-isothiazoline-3-one and mixtures thereof.

4. The solution of claim 3, wherein the preservative is diazolidinyl urea or a mixture of 5-chloro-2-methyl-4-isothiazolin-one and 2-methyl-4-isothiazoline-3-one.

5. The solution of claim 1, further comprising a buffer.

6. The solution of claim 5, wherein the buffer is selected from the group consisting of a citrate buffer, an imidazole buffer and a N-2-hydroxyethyl piperazine-N-2-ethanesulfonic acid buffer.

7. The solution of claim 1, further comprising a viscosity enhancer.

8. The solution of claim 7, wherein the viscosity enhancer is glycerol, polyvinylpyrrolidone or a combination thereof.

9. The solution of claim 1, further comprising:
   a) a citrate buffer or a N-2-hydroxyethyl piperazine-N-2-ethanesulfonic acid buffer;
   b) glycerol, polyvinylpyrrolidone, or a combination thereof; and
   c) diazolidinyl urea, or a combination of 5-chloro-2-methyl4-isothiazolin-one and 2-methyl-4-isothiazoline-3-one.

* * * * *